United States Patent

Lenz et al.

[11] Patent Number: 6,060,285
[45] Date of Patent: *May 9, 2000

[54] PROCESS FOR THE PRODUCTION OF HETERO-BISPECIFIC ANTIBODIES

[75] Inventors: Helmut Lenz, Tutzing; Ulrich Weidle, München, both of Germany

[73] Assignee: Roche Diagnostics GmbH, Mannheim, Germany

[*] Notice: This patent is subject to a terminal disclaimer.

[21] Appl. No.: 07/500,596

[22] Filed: Mar. 22, 1990

[30] Foreign Application Priority Data

Mar. 23, 1989 [DE] Germany ............... 39 09 708

[51] Int. Cl.$^7$ ............ C07H 15/12; C12P 21/06; C12N 15/00; C12N 5/00
[52] U.S. Cl. ............ 435/69.6; 435/172.3; 435/240.27; 435/320.1; 435/972; 536/23.53
[58] Field of Search ............ 536/27, 23.53; 435/320.1, 69.6, 240.27, 172.3, 972

[56] References Cited

U.S. PATENT DOCUMENTS 4,474,893 10/1984 Reading et al. ............ 436/547

OTHER PUBLICATIONS

Choo et al. DNA vol. 5(6) 529–537 (1986) Vectors for Expression and Amplification of cDNA Morrison et al., PNAS 81:6851–6855 (1984) Chimeric human antibody molecules . . . .

Primary Examiner—David L. Lacey
Assistant Examiner—T. Michael Nisbet
Attorney, Agent, or Firm—McCormick, Paulding & Huber

[57] ABSTRACT

For the production of hetero-bispecific monoclonal antibodies at least the genes for the light chain and for the variable part of the heavy chain are isolated from a hybridoma cell line which secretes an antibody with a desired specificity and they are inserted into a eukaryotic plasmid vector which contains a marker capable of selection together with a strong promoter, this expression vector is transfected into a hybridoma cell line which secretes antibodies with a second desired specificity, the cell line is cultured, the antibodies are obtained and the bispecific antibody is isolated.

19 Claims, 2 Drawing Sheets a)

PROCESS FOR THE PRODUCTION OF HETERO-BISPECIFIC ANTIBODIES

Description

The invention concerns a process for the production of hetero-bispecific antibodies.

Hetero-bispecific or also heterobifunctional antibodies are antibodies which have two different antigen binding sites i.e. they are directed towards two different epitopes. Heterobifunctional antibodies could be used for the therapy of diseases. Thus a bispecific antibody can have e.g. an antigen binding site for a cell-surface antigen of a cancer cell and an antigen binding site for a particular drug. In this way, a therapeutic agent can then be targeted specifically to a cancer cell. Another variant is a bispecific antibody one of whose antigen binding sites is directed towards a T-cell surface antigen and its other antigen binding site is directed towards an antigenic determinant of a virus. Such an antibody would enable the specific destruction of viruses in blood.

Processes for the production of bispecific antibodies are already known. Thus in Proc. Natl. Acad. Sci., USA, 83 (1986), 4479–4483 and in Eur. J. Immunol., 17 (1987), 571–574 a process is described in which two different antibodies are chemically bound together using a spacer. This process is, however, complicated and results in a new topographical configuration of the antibodies.

Furthermore, a process is known from Proc. Natl. Acad. Sci., USA, 83 (1986), 1453–1457 in which two cell lines which each secrete different antibodies are fused together. In this process hybridoma cells are formed which contain the double set of chromosomes and produce the desired heterobifunctional antibodies. A disadvantage of this process is that the cell lines obtained are frequently not stable and therefore unsuitable for the production of heterobifunctional antibodies on an industrial scale.

It was therefore the object of the present invention to provide a process by which bispecific antibodies can be isolated in good yields and which can be carried out on an industrial scale.

This object is achieved by a process for the production of bispecific monoclonal antibodies which is characterized in that at least the genes for the light chain and the variable part of the heavy chain are isolated from a hybridoma cell line which secretes an antibody with a desired specificity and are inserted into a eukaryotic plasmid vector, this expression vector is transfected into a hybridoma cell line which secretes antibodies with a second desired specificity, the cell line is cultured, the antibodies are obtained and the bispecific antibody is isolated.

Surprisingly, it is possible to obtain bispecific antibodies in large yields using the process according to the present invention. The transfected hybridoma cell lines used according to the present invention secrete homobifunctional antibodies which are coded by the genome of the hybridoma cell line and the expression vector, as well as heterobifunctional antibodies formed from the genes of both antibodies which have an antigen binding site of the hybridoma host cell and an antigen binding site of the transfected vector. Surprisingly the yield of this heterobifunctional antibody is very high. Apart from the two homofunctional antibodies, the heterobifunctional antibody can be determined in a simple way e.g. by binding to one of its antigens which is fixed to a solid phase and binding to the other antigen which is labelled and used in a soluble form.

For the production of the bispecific antibodies according to the present invention, a eukaryotic expression vector is introduced into a hybridoma cell line. The main elements contained in the eukaryotic expression vector are a marker capable of selection, a strong promoter and the gene for the expression of a complete or incomplete antibody. Many different eukaryotic plasmid vectors are suitable for the insertion of immunoglobulin genes and are known to the expert. The following vectors are for example suitable:

a) Vectors which express the phosphotransferase neo in which transformants are selected by the antibiotic G418. These vectors are described by P. Southern and P. Berg, J. Mol. Appl. Genet. 1 (1982), 327–341.

b) Vectors which express the *E. coli* xanthine-guanine phosphoribosyltransferase in which the transformants are selected on the basis of resistance to mycophenolic acid. These vectors are described by R. Mulligan and P. Berg in Proc. Natl. Acad. Aci. USA, 78 (1981), 2072–2076.

c) Vectors which express multi-drug resistance genes. The selection is effected in this case with drugs such as e.g. colchicin, vinblastin, adriamycin or actinomycin D. These vectors are described by S. E. Kane, B. R. Troen, S. Gal, K. Keda, I. Pastan and M. M. Gottesman, Mol. and Cell. Biol. 8 (1988), 3316–3321 as well as by D. W. Shou, A. Fojo, I. B. Roninson, J. E. Chin, R. Soffir, I. Pastan and M. M. Gottesman, Mol. and Cell. Biol. 6 (1986), 4039–4044.

d) Vectors which express dihydrofolate reductase or a mutant with a reduced affininity for methotrexate. The transformants are selected by growing them in media containing methotrexate. The vectors are described by R. Kaufman and P. A. Sharp, J. Mol. Biol. 159 (1982), 601–621 and by C. C. Simonson et al., Proc. Natl. Acad. Sci., USA 80, (1983), 2495–2499.

These vectors all already have a marker capable of selection. The plasmid pMT010/A$^+$ can for example be used as the starting vector.

Immunoglobulin genes which code for at least the variable part and the $c_H1$ domain of an antibody of the desired specificity or for a complete antibody are inserted into the vector in a well-known way. In this process, the corresponding DNA can either be isolated from a hybridoma which produces antibodies of the desired specificity and ligated into the vector or the genomic DNA of the desired immunoglobulin gene can be used (cf. Buckel et al., Gene 51 (1980) 13–19).

At least the gene for the light chain, the variable part of the heavy chain and the $c_H1$ domain of the desired antibody are used as immunoglobulin genes.

The gene for the light chain can be the gene for a or for a chain. The complete gene is used in each case. The choice of the gene for the heavy chain depends on the type of the desired antibody. According to the class of the antibody the gene is chosen from the $\mu$, $\gamma1$, $\gamma2$, $\gamma3$, $\gamma4$, $\alpha1$, $\alpha2$, $\zeta$ or $\epsilon$ chain. Either the entire information for the heavy chain can be used for this or only part of the DNA encoding the heavy chain. If necessary, depending on the desired class of the antibody to be produced as well as on the hybridoma cell line used, the $c_H2$, $c_H3$ as well as, if desired, the $c_H4$ domain are chosen. If the bispecific antibodies produced according to the present invention are to be used for the therapeutic treatment of humans then it is preferable to use DNA of the $c_H1$, $c_H2$, $c_H3$ and if desired $c_H4$ domain of human immunoglobulin.

In an embodiment of the process according to the present invention an expression vector is used which contains a $\lambda$ gene for the light chain and a $\gamma_1$ gene of a mouse or human antibody.

A preferred component of the eukaryotic expression vector is a strong promoter. Promoters which generate a high rate of production are known to the expert. The early or late promoter of SV40, immunoglobulin promoters for light and heavy chains, the immediate-early cytomegalo-virus promoter as well as the metallothionein promoter are for example suitable. Equally suitable are other constitutive viral or cellular promoters.

The eukaryotic expression vector thus composed is transfected into a hybridoma cell line which secretes antibodies with antigen binding sites A. Hybridoma cell lines which produce antibodies with the desired binding site are suitable for this. A hybridoma cell line is preferably used which produces antibodies of the same class as that from which the antibodies to be produced originate. Particularly suitable are mouse or human hybridoma cell lines.

The transfection of the expression vector into the hybridoma cell line is carried out in a well-known way. The transfection is preferably performed by electroporation (Nucleic Acids Res. 15 (1987) 1311–1326; Bio Techniques 6 (1988) 742–751).

The cell lines thus obtained are selected by means of the corresponding markers, cultured and the antibodies are then isolated according to well-known methods (e.g. A. Y. Liu, et al., Proc. Natl. Acad. Sci. USA 84 (1987) 3439; S. L. Morrison et al., Proc. Natl. Acad. Sci. USA 81 (1984) 6851).

The transfected cell lines produce the homobifunctional antibody which is secreted by the host hybridoma cell line as well as the homobifunctional antibody which is encoded by the eukaryotic expression vector as well as a heterobifunctional antibody which has two different antigen binding sites. If the transfected expression vector only contains the information for the variable regions of an antibody with the antigen binding site B, then antibody halves formed with specificity B are such that their constant part corresponds to that of the antibody coded by the host cell so that the bispecific antibodies which are formed on assembly of two such antibody halves have the antigen binding sites A and B and the constant part of the antibody produced by the host hybridoma cell.

This interpretation of the formation of the heterobifunctional antibodies does not, however, exclude other possible ways of formation and thus only represents one attempt at an explanation.

The heterobifuntional antibody is secreted in a surprisingly high yield. It was found that the formation of the desired antibody is increased by a factor of 10 compared to non-immunoglobulin producer hybridoma cells transfected with expression constructs for light and heavy chains of a monoclonal antibody. This means that the cell lines prepared according to the present invention have an about 10-fold increased antibody production rate.

The desired antibody can be isolated according to well-known methods from the culture supernatant which contains a mixture of ten different kinds of antibodies (all possible combinations of the light and heavy chains of both antibodies). The desired antibody is preferably isolated by immunosorption. In a particularly preferred embodiment the isolation of the bifunctional antibody is carried out in two steps. At first the solution containing all kinds of antibodies is brought into contact with an antigen capable of binding to the antigen binding site A whereby the antibodies A and AB are adsorbed. After elution of the bound antibodies the heterobifunctional antibody is selectively isolated from the homobifunctional antibody in a second step from the solution containing the homo- and bifunctional antibodies by adsorption with an antigen capable of binding to the antigen binding site B. The hetero-bifunctional antibodies can be eluted in a highly purified form.

A process is made available according to the present invention with which heterobifunctional antibodies can be obtained in an excellent yield. These antibodies are especially suitable for use in cancer therapy or in diseases caused by viruses. The desired antigenic determinants can be chosen according to the application. The therapist therefore has a wide field from which he can choose the respective best combination of the two antigenic determinants. Furthermore, it is also possible to vary the Fc part of the antibody which is responsible for different biological processes.

The invention is elucidated by the following Figures and Examples:

The plasmids pBMS1 (DSM 5229) and pBMS2 (DSM 5230) as well as the microorganism E. coli HB101 (DSM 1607) are deposited at the German Collection of Microorganisms. The hybridoma cell line MAK33 is deposited at the European Collection of Animal Cell Cultures under the number ECACC 88091404.

EXAMPLE 1
Isolation of Immunoglobulin Genes

The $\lambda$ and $\gamma_1$ genes of the monoclonal antibody were isolated as described by F. Sablitzky, G. Wildner and K. Rajewsky, EMBO J. 4 (1985) 345–350 and Chr. Kocks and K. Rajewsky, Proc. Natl. Acad. Sci. USA (1988) 85, 8206–8210 from the mouse hybridoma line A20/44 which secretes anti-idiotypic antibodies (antibody B) directed against monoclonal mouse $\lambda$, $\gamma_{2a}$ anti-nitrophenol antibody.

The active genes were provided with SalI linkers (CGTCGACG) and subcloned in pUC18 or pBR322. The gene for the light chain was encoded on a 5.5 kb fragment, the gene for the heavy chain on a 9.25 kb fragment.

Figure 1:
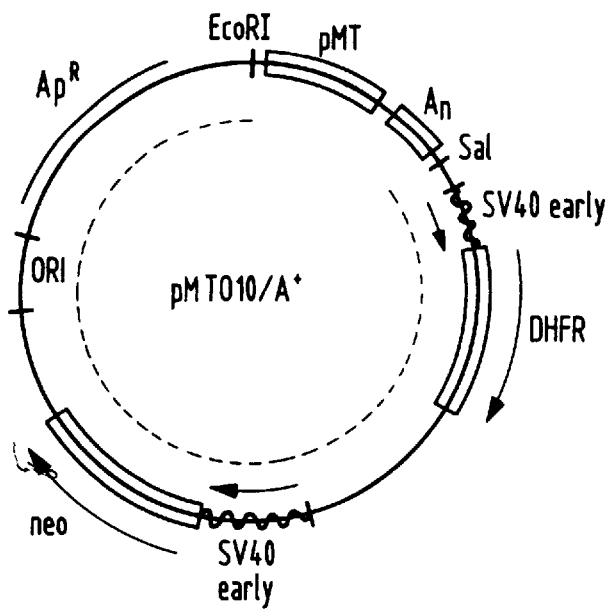
FIG. 1 shows the pre-construction for the expression plasmids.
Figure 1:
Figure 1:
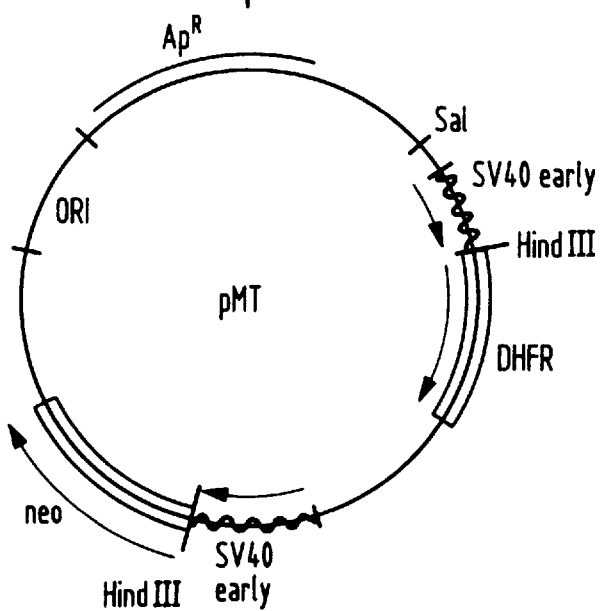

EXAMPLE 2
Construction of an Expression Vector for Immunoglobulin Genes pMTO10/A$^+$ was used as the starting plasmid (DNA 5 (1986) 529–537). This plasmid contains a sheep metallothionein promoter (pMT) with a subsequent polyadenylation site ($A_n$), an expression cassette for the mouse dihydrofolate reductase gene under the control of the early promoter of SV40, an expression cassette for the phosphotransferase neo under the control of the early promoter of SV40, a bacterial origin of replication and a gene which codes for ampicillin resistance. The sheep metallothionein promoter with its polyadenylation site was cut out by cleavage of the plasmid with EcoRI and SalI, the fragments were treated with nuclease S1 and the fragment of FIG. 1 marked by a dotted line was isolated from a low-melting agarose gel. Subsequently SalI linkers were ligated on, cut again with SalI, the fragment provided with a linker was isolated on a low-melting agarose gel, re-ligated (T4 ligase), transfected into E. coli HB101 (DSM 1607) and ampicillin resistant colonies were isolated. Plasmid pMT was characterized by restriction analysis (two fragments of 2.8 and 4.65 kb were obtained by cleavage with HindIII). The $\lambda$ gene from the hybridoma line A20/44, which was provided with SalI cleavage sites at the ends, was ligated into the SalI site of plasmid pMT. The plasmid obtained was partially cleaved with SalI and the $\gamma_1$ gene from the hybridoma cell line pA20/44 was ligated in as a 9.25 kb Sal fragment.

Figure 2:
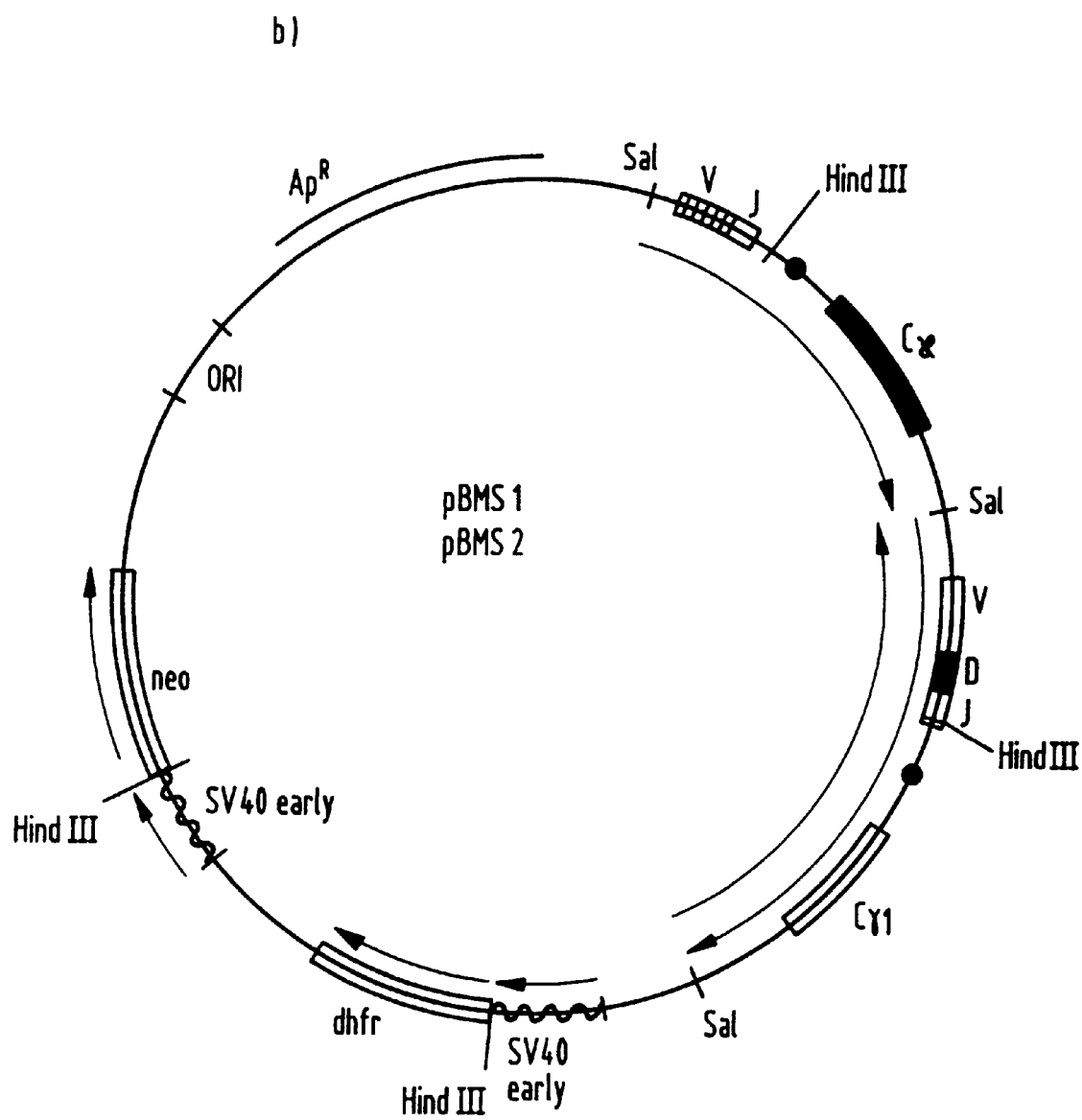
FIG. 2 shows the expression vectors used.

The plasmids pBMS1 and pBMS2 which thereby form correspond to the different orientations of the $\gamma_1$ gene with respect to the $\varkappa$ gene (FIG. 2). Cleavage of plasmid pBMS1 with HindIII resulted in fragments of 8.6, 6.6, 4.2 and 2.8 kb; cleavage of plasmid pBMS2 with HindIII resulted in fragments of 11.5, 6.6, 2.8 and 1.3 kb.

EXAMPLE 3
Transfection of a Producer Hybridoma Cell Line with Expression Constructs for Immunoglobulin Genes.

The plasmids pBMS1 and pBMS2 were introduced into the hybridoma line MAK33 (ECACC 88091404) described by Buckel et al., Gene 51 (1980) 13–19, which secretes antibodies (antibody A) directed towards the M subunit of creatine kinase by electroporation (Gene Pulser by Bio-Rad) according to the methods described in Nucleic Acids Res. 15 (1987) 1311–1326 or Bio Techniques 6 (1988) 742–751. 10 $\mu$g of plasmid-DNA and $1\times10^6$ cells were used per pulse.

The cells were centrifuged down, then washed with cold HeBS buffer (20 mM HEPES, pH 7.05, 137 mM NaCl, 5 mM KCl, 0.7 mM $Na_2HPO_4$, 6 mM dextrose), resuspended in HeBS buffer, adjusted to a concentration of $10^6$ cells/ml and placed on ice. After addition of plasmid they were pulsed (conditions: capacitance 500 $\mu$F and voltage range between 240 and 350 V or at 160 $\mu$F and 200 to 260 V). After pulsing for about 10 minutes the cells were kept on ice and subsequently incubated at 37° C. in medium I (RPMI 1640, 10% foetal calf serum, 2 mmol/l glutamine, 1 mmol/l sodium pyruvate, 0.1 mol/l non-essential amino acids).

The selection of stable transformants was effected by incubation with a medium containing G418 at a concentration of 800 $\mu$g G418/ml medium.

Stable transformants were identified after about 14 days and were isolated by "limited dilution" and propagated in mass culture in medium I.

EXAMPLE 4
Determination of Immunoreactive Protein in the Supernatants

The determination was carried out with an ELISA test as described in Gene 56 (1987) 205–216. For the determination of the kappa chains, microtitre plates were coated with anti-mouse IgG antibodies from sheep and incubated with supernatants of the transfected cells. After washing a conjugate of peroxidase and of Fab fragments of a sheep antibody (IgG) which was directed towards mouse Fab fragments (IgG) was added. Subsequently ABTS (2,2-azino-di-[3-ethyl-2,3-benzothiazole-6-sulphonate]) was added as substrate for peroxidase and the colour formed was measured at 405 nm as a measure for the amount of kappa chain present in the solution.

The gamma chains were determined in an analogous way, in which, however, a conjugate of peroxidase and Fab fragments of an antibody from sheep (IgG) which was directed towards mouse Fc-gamma (IgG) was used for detection.

EXAMPLE 5
Isolation of the Antibodies

The culture supernatants containing antibodies with specificity A, B and AB were chromatographed on an affinity column on which antigen capable of binding to the antibody A was bound. In this way antibody B could be separated off. Antibody A and the hybrid antibody AB were bound to the immobilized antigens. Subsequently the antibodies A and the hybrid antibodies AB were eluted with a solution of 0.2 mol/l glycine, pH 2.8 and the eluate was chromatographed on an affinity column on which antigen capable of binding to antibody B was immobilized. Antibody A was present in the liquid which flowed off the column, antibody AB was bound selectively and was obtained in pure form by elution with a solution of 0.2 mol/l glycine, pH 2.8.

Definition of the Antibodies
Antibody A:
  CK-MM specific antibody of the hybridoma line MAK33
Antibody B:
  Anti-idiotypic antibody from cell line A20/44 according to Example 1
Antibody AB:
  Hybrid antibody from antibodies A and B

EXAMPLE 6
Preparation of Biotinylated CK-MM

CK-MM (creatine kinase, EC 2.7.3.2.) was isolated from human skeletal muscle according to Keutel et al., Arch. Biochem. Biophys. 150 (1972) 648. 0.43 $\mu$mol biotinyl-$\epsilon$-aminocaproic acid-N-hydroxysuccinimide ester in 50 $\mu$l dimethylsulphoxide was pipetted into a solution of 10 mg CK-MM (0.12 $\mu$mol) in 30 mM potassium phosphate buffer pH 7.1 and incubated for 60 minutes in an ice bath. Subsequently the excess reagent was removed by dialysis against 2 mM carbonate buffer, pH 8.7 and the biotinylated CK-MM was lyophilized.

EXAMPLE 7
Specific Determination of the Hybrid Antibody AB in the Culture Supernatants.

The wells of a microtitre plate were coated with thermo-BSA-streptavidin (10 $\mu$g/ml in 40 mmol/l potassium phosphate, pH 7.4 (prepared according to EP-A 0 269 092)). After re-coating with buffer I (50 mmol/l HEPES, 0.15 mol/l NaCl, 1% crotein C, pH 7.0) they were coated with biotinylated human CK-MM (prepared according to Example 6) (1 $\mu$g/ml in buffer I). Afterwards they were incubated for one hour at room temperature with the cell culture supernatants which contained the hybrid MAB AB and subsequently they were washed twice with incubation buffer (composition: 50 mmol/l HEPES, pH 7.0, 0.15 mol/l NaCl, 1% crotein C, 0.2 mol/l di-sodium tartrate, 0.75% PEG 40000, 0.5% Pluronic F68, 0.01% phenol). Afterwards they were incubated with POD-labelled Fab fragments (127 mU/ml POD activity) of an antibody (antibody C) directed towards the antibody B. Residual conjugate was removed by washing three times with 50 mmol/l HEPES, pH 7.0, 0.15 mmol/l NaCl, 0.1% Pluronic F68. ABTS (2,2'-azino-di-[3-ethyl-2,3-benzothiazole-6-sulphonate]) was added as a substrate for POD for the determination of the label, incubated for one hour and subsequently the absorption was measured at 405 nm in a photometer (ELISA-reader). A calibration curve was established with a model hybrid antibody which was obtained by cross-linking antibody B with Fab fragments of antibody A. The concentrations of the standard used were from 0 to 11.5 ng/ml.

EXAMPLE 8
Determination of Antibody B

Microtitre plates were coated with antibody C (directed against nitrophenol). The coating buffer consisted of 0.2 mmol/l carbonate/bicarbonate, pH 9.4. After 2 hours the plates were incubated for 30 minutes with a re-coating buffer (50 mmol/l HEPES, 0.15 mol/l NaCl, 1% crotein C, pH 7.0). All reactions were carried out at room temperature with shaking. The calibration curve was established with a standard solution containing antibody B. The calibration samples and the cell culture supernatants were diluted with medium I and incubated for 2 hours at room temperature.

After aspirating the wells and washing twice with incubation buffer (50 mmol/l HEPES, 0.15 mmol/l NaCl, 0.2 mol/l di-sodium tartrate, 1% crotein C, 0.75% PEG 40000, 0.5% Pluronic F68, 0.01% phenol, pH 7.0) they were incubated with conjugate for one hour. A conjugate of Fab fragments of antibody C and POD was used for this which was diluted in incubation buffer to 159 mU/ml POD activity. After aspirating and washing three times with washing buffer (50 mmol/l HEPES, 0.15 mmol/l NaCl, 0.1% Pluronic F68, pH 7.0) they were reacted for 60 minutes with ABTS as substrate. The absorption was measured at 405 nm against 490 nm in a photometer (ELISA-reader). The concentrations of the samples were determined using the standard calibration curve.

EXAMPLE 9

Determination of Antibodies A and AB

Thermo-BSA-streptavidin (10 μg/ml) in coating buffer (40 mmol/l potassium phosphate buffer, pH 7.4) was adsorbed onto a solid phase (microtitre plate with 96 wells, Nunc). Unbound streptavidin was carefully removed and unspecific binding sites were saturated with re-coating solution (50 mmol/l potassium phosphate buffer, 0.15 mol/l NaCl, 1% BSA, pH 7.5). Before application, the calibration samples (antibody A=CK-MM specific) and the culture supernatants were diluted 1:10 with biotinylated CK-MM (500 ng/ml) obtained according to Example 6. After incubation of the samples for one hour they were washed twice with the above-mentioned incubation buffer. Subsequently they were incubated for one hour with POD-labelled polyclonal antibody directed towards the Fc part of mouse IgG (POD activity 130 mU/ml) prepared in goats. After incubation with the substrate ABTS the absorption was measured at 405 nm in a photometer (ELISA-reader).

The content of antibody A was determined by subtracting the concentrations of antibodies (A+AB) and antibody (AB).

EXAMPLE 10

Determination of Antibodies B and AB

Microtitre plates were coated with 10 μg/ml sheep IgG in 0.2 mol/l bicarbonate/carbonate buffer (pH 9.5) directed towards the Fc γ part of mouse IgG. Unbound antibody was removed and the non-specific binding sites were saturated with re-coating solution (50 mmol/l potassium phosphate buffer, 0.15 mol/l NaCl, 1% BSA (bovine serum albumin), pH 7.5). All reactions were carried out at room temperature with shaking. The culture supernatants were diluted with 50 mmol/l potassium phosphate, pH 7.5, 0.2 mol/l sodium tartrate, 1% BSA and incubated for one hour. After washing twice with incubation buffer they were incubated with a conjugate of POD and Fab fragments of antibody C (POD activity 130 mU/ml). After washing they were incubated with ABTS and the absorption was measured after 60 minutes at 405 nm in a photometer (ELISA-reader). A calibration curve was established with purified antibody B.

The content of antibody B was calculated by subtracting the concentration of antibody B+AB and antibody AB.

EXAMPLE 11

Comparison of the Yields of Antibodies A, B and AB

The plasmid pBMS1 was transfected into the cell line MAK33 which produces the antibody A which is specific for CK-MM, colonies resistant to G418 were isolated and the following parameters were determined in 24-hour supernatants after inoculation of $10^6$ cells.

a) antibody AB
b) antibody B
c) antibody A

The results are shown in Table 1

TABLE 1

| Cell line | Antibody A (μg/ml) | Antibody AB (μg/ml) | Antibody B (μg/ml) |
|---|---|---|---|
| 1  | 9    | 2, 2 | 0, 2  |
| 2  | 6, 5 | 2, 7 | 0, 3  |
| 3  | 7    | 2, 3 | 0, 1  |
| 4  | 4, 8 | 2, 2 | 0, 3  |
| 5  | 7    | 2, 5 | 0, 2  |
| 6  | 11, 8| 0, 7 | 0, 05 |
| 7  | 7    | 1, 6 | 0, 3  |
| 8  | 5    | 1    | 0, 1  |
| 9  | 11   | 0, 6 | 0, 05 |
| 10 | 9    | 1, 8 | 0, 3  |
| 11 | 5, 4 | 3    | 0, 3  |
| 12 | 7    | 0, 8 | 0, 1  |

Similar results were obtained using plasmid pBMS2.

What is claimed is:

1. Process for the production of hetero-bispecific monoclonal antibodies with an antigen binding site A and an antigen binding site B, wherein at least the genes for the light chain, for the variable part of the heavy chain, as well as the $c_H1$ domain are isolated from a hybridoma cell line which secretes an antibody with antigen binding site A and are inserted into a eukaryotic plasmid vector, this expression vector is transfected into a hybridoma cell line which secretes antibodies with antigen binding site B, the cell line is cultured, the antibodies are obtained and the bispecific antibody is isolated.

2. Process as claimed in claim 1, wherein one transfects with a eukaryotic expression vector which contains the entire genetic information for a complete antibody.

3. Process as claimed in claim 1, wherein an expression vector is used which contains the K gene as well as the gene for the γ, chain of a mouse antibody.

4. Process as claimed in claim 1, wherein an expression vector is used which contains a marker capable of selection and a strong promoter.

5. Process as claimed in claim 1, wherein plasmid pBMS1 (DSM 5229) or pBMS2 (DSM 5230) is used as the expression vector.

6. Process as claimed in claim 1, wherein the early or late promoter of SV40, the cytomegalo-virus immediate-early promoter or the metallothionein promoter is used as the promoter.

7. Process as claimed in claim 1, wherein the transfection of the hybridoma cell line with the eukaryotic expression vector is effected by electroporation.

8. Process according to claim 2 wherein the early or late promoter of SV40, the cytomegalo-virus immediate-early promoter or the metallothionein promoter is used as the promoter.

9. Process according to claim 3 wherein the early or late promoter of SV40, the cytomegalo-virus immediate-early promoter or the metallothionein promoter is used as the promoter.

10. Process according to claim 4 wherein the early or late promoter of SV40, the cytomegalo-virus immediate-early promoter or the metallothionein promoter is used as the promoter.

11. Process according to claim 5 wherein the early or late promoter of SV40, the cytomegalo-virus immediate-early promoter or the metallothionein promoter is used as the promoter.

12. Process according to claim 2 wherein the transfection of the hybridoma cell line with the eukaryotic expression vector is effected by electroporation.

13. Process according to claim 3 wherein the transfection of the hybridoma cell line with the eukaryotic expression vector is effected by electroporation.

14. Process according to claim 4 wherein the transfection of the hybridoma cell line with the eukaryotic expression vector is effected by electroporation.

15. Process according to claim 5 wherein the transfection of the hybridoma cell line with the eukaryotic expression vector is effected by electroporation.

16. Process according to claim 8 wherein the transfection of the hybridoma cell line with the eukaryotic expression vector is effected by electroporation.

17. Process according to claim 9 wherein the transfection of the hybridoma cell line with the eukaryotic expression vector is effected by electroporation.

18. Process according to claim 10 wherein the transfection of the hybridoma cell line with the eukaryotic expression vector is effected by electroporation.

19. Process according to claim 11 wherein the transfection of the hybridoma cell line with the eukaryotic expression vector is effected by electroporation.

* * * * *